US009568485B2

(12) United States Patent (10) Patent No.: US 9,568,485 B2
Seidmann et al. (45) Date of Patent: Feb. 14, 2017

(54) METHOD FOR THE EARLY DIAGNOSIS OF CLINICALLY LATENT PLACENTAL INSUFFICIENCY ASSOCIATED WITH DEFECTIVE PLACENTAL MATURATION

(75) Inventors: Larissa Seidmann, Mainz (DE); Charles James Kirkpatrick, Dexheim (DE)

(73) Assignee: Universitaetsmedizin der Johannes Gutenberg-Universitaet Mainz, Mainz (DE)

( * ) Notice: Subject to any disclaimer, the term of this patent is extended or adjusted under 35 U.S.C. 154(b) by 178 days.

(21) Appl. No.: 14/233,601

(22) PCT Filed: Jul. 20, 2012

(86) PCT No.: PCT/EP2012/064354
§ 371 (c)(1),
(2), (4) Date: May 20, 2014

(87) PCT Pub. No.: WO2013/014112
PCT Pub. Date: Jan. 31, 2013

(65) Prior Publication Data
US 2014/0249080 A1 Sep. 4, 2014

(30) Foreign Application Priority Data

Jul. 22, 2011 (EP) ..................................... 11006020

(51) Int. Cl.
*C12Q 1/68* (2006.01)
*G01N 33/74* (2006.01)
*A61K 38/28* (2006.01)
*A61K 45/06* (2006.01)
*G01N 33/68* (2006.01)

(52) U.S. Cl.
CPC .............. *G01N 33/74* (2013.01); *A61K 38/28* (2013.01); *A61K 45/06* (2013.01); *C12Q 1/6883* (2013.01); *G01N 33/689* (2013.01); *C12Q 2600/118* (2013.01); *C12Q 2600/158* (2013.01)

(58) Field of Classification Search
CPC ................................................... C12Q 1/6883
See application file for complete search history.

(56) References Cited

PUBLICATIONS

Alfaidy, 2016, Prokinecticin 1 and pregnancy, 77(2): abstract only.*
Alfaidy et al., 2014, The Multiple Roles of EG-VEGF/PROK1 in Normal and Pathological Placental Angiogenesis, BioMed Research International, 2014: 10 pages.*
Seidmann et al., 2013, Imbalance of expression of bFGF and PK1 is associated with defective maturation and antenatal placental insufficiency, European Journal of Obstetrics & Gynecology and Reproductive Biology, 170: 352-357.*
Brouillet et al., 2013, EG-VEGF controls placental growth and survival in normal and pathological pregnancies: case of fetal growth restriction (FGR).*
Catalano, Rob D. et al., "Prokineticins: novel mediators of inflammatory and contractile pathway at parturition?" *Molecular Human Reproduction*, 2010, vol. 14, No. 5, p. 311-319.
Hoffmann, Pascale et al., "Expression and Oxygen Regulation of Endocrine Gland-Derived Vascular Endothelial Growth Factor/Prokineticin-1 and Its Receptors in Human Placenta during Early Pregnancy," *Endocrinology*, 2006, vol. 147, No. 4, p. 1675-1684.
Ngan, Elly S.W. and Tam, Paul H.K., "Prokineticin-signaling pathway," *The International Journal of Biochemistry and Cell Biology*, 2008, vol. 40, p. 1679-1684.
Shaw, Julie L.V. et al., "Evidence of prokineticin dysregulation in Fallopian tube from women with ectopic pregnancy," *Fertil Steril*, Oct. 2010, vol. 94, No. 5, p. 1601-1608.
Su, Mei-Tsz etal., "Polymorphisms of endocrine gland-derived vascular endothelial growth factor gene and its receptor genes are associated with recurrent pregnancy loss," *Human Reproduction*, 2010, vol. 25, No. 11, p. 2923-2930.

* cited by examiner

*Primary Examiner* — Amber D Steele
(74) *Attorney, Agent, or Firm* — Saliwanchik, Lloyd & Eisenschenk

(57) ABSTRACT

The present invention relates to a method for the early diagnosis of a clinically latent placental insufficiency in pathological placental maturation, and the prophylaxis of an intrauterine fetal hypoxia/asphyxia at the due date or after a prolonged gestation, comprising determining the amount and/or the concentration of the biomarker prokineticin 1 (EG-VEGF) and/or its receptor PKR1 and/or PKR2 in a sample from the pregnant subject and/or the pregnancy. In a preferred embodiment, the invention is based on determining the ratio of the amount and/or the concentration of bFGF/PK1 as a measure of current functional condition and an indicator of latent clinical problems such as placental dysfunction resulting in fetal hypoxia.

Figure 1:
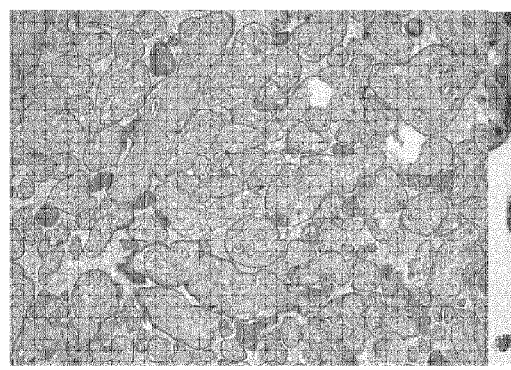
Figure 1:
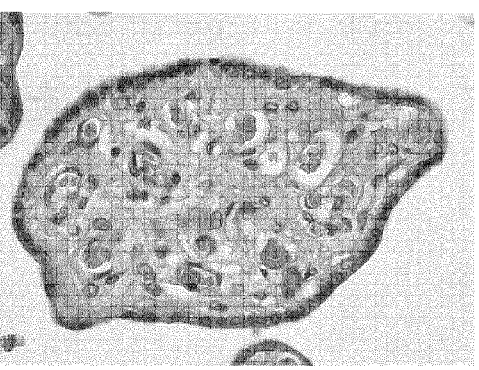
Figure 1:
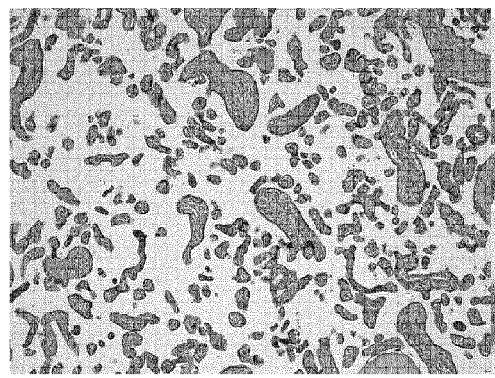
Figure 1:
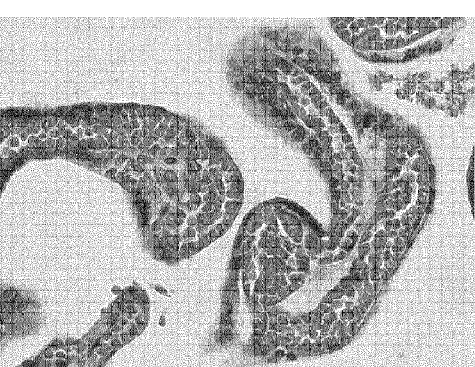

19 Claims, 5 Drawing Sheets a)  b)

c)  d)

■ Severe and medium placental insufficiency with fetal hypoxia without intrauterine death ▨ Severe and medium placental insufficiency with fetal hypoxia and intrauterine death ☐ Low-grade placental insufficiency with compensatory hypervascularization (angiosis type II) and fetal hypoxia without intrauterine death

SEQUENCE LISTING

<160> NUMBER OF SEQ ID NOS: 16

<210> SEQ ID NO 1
<211> LENGTH: 19
<212> TYPE: DNA

-continued

```
<213> ORGANISM: Homo sapiens

<400> SEQUENCE: 1
atggggaagg tgaaggtcg                                              19

<210> SEQ ID NO 2
<211> LENGTH: 20
<212> TYPE: DNA
<213> ORGANISM: Homo sapiens

<400> SEQUENCE: 2
taaaagcagc cctggtgacc                                             20

<210> SEQ ID NO 3
<211> LENGTH: 23
<212> TYPE: DNA
<213> ORGANISM: Homo sapiens

<400> SEQUENCE: 3
cctggaggag aagaggaaag aga                                         23

<210> SEQ ID NO 4
<211> LENGTH: 21
<212> TYPE: DNA
<213> ORGANISM: Homo sapiens

<400> SEQUENCE: 4
ttcgtagcct catgagctgt t                                           21

<210> SEQ ID NO 5
<211> LENGTH: 18
<212> TYPE: DNA
<213> ORGANISM: Homo sapiens

<400> SEQUENCE: 5
cgagggcctg gagtgtgt                                               18

<210> SEQ ID NO 6
<211> LENGTH: 21
<212> TYPE: DNA
<213> ORGANISM: Homo sapiens

<400> SEQUENCE: 6
ccgcataatc tggatggtga t                                           21

<210> SEQ ID NO 7
<211> LENGTH: 22
<212> TYPE: DNA
<213> ORGANISM: Homo sapiens

<400> SEQUENCE: 7
ccgttacctg cctatgaagg aa                                          22

<210> SEQ ID NO 8
<211> LENGTH: 26
<212> TYPE: DNA
<213> ORGANISM: Homo sapiens

<400> SEQUENCE: 8
aaagaaacac tcatccgtaa cacatt                                      26

<210> SEQ ID NO 9
<211> LENGTH: 22
```

-continued

<212> TYPE: DNA
<213> ORGANISM: Homo sapiens

<400> SEQUENCE: 9
gcgatgagaa tctgcactgt gt                                           22

<210> SEQ ID NO 10
<211> LENGTH: 21
<212> TYPE: DNA
<213> ORGANISM: Homo sapiens

<400> SEQUENCE: 10
tccccagaac ggatctttag g                                            21

<210> SEQ ID NO 11
<211> LENGTH: 22
<212> TYPE: DNA
<213> ORGANISM: Homo sapiens

<400> SEQUENCE: 11
cgcgagtctc aatcatgctc ct                                           22

<210> SEQ ID NO 12
<211> LENGTH: 22
<212> TYPE: DNA
<213> ORGANISM: Homo sapiens

<400> SEQUENCE: 12
ggcaaggcgc taaaaattga tg                                           22

<210> SEQ ID NO 13
<211> LENGTH: 24
<212> TYPE: DNA
<213> ORGANISM: Homo sapiens

<400> SEQUENCE: 13
tgccttctac atcgtccagt gcat                                         24

<210> SEQ ID NO 14
<211> LENGTH: 24
<212> TYPE: DNA
<213> ORGANISM: Homo sapiens

<400> SEQUENCE: 14
tgtaagaagc cttccagtgg agca                                         24

<210> SEQ ID NO 15
<211> LENGTH: 24
<212> TYPE: DNA
<213> ORGANISM: Homo sapiens

<400> SEQUENCE: 15
tctgcggcat cggtaacttt gtct                                         24

<210> SEQ ID NO 16
<211> LENGTH: 24
<212> TYPE: DNA
<213> ORGANISM: Homo sapiens

<400> SEQUENCE: 16
caggttggca atgagcagat tggt                                         24

METHOD FOR THE EARLY DIAGNOSIS OF CLINICALLY LATENT PLACENTAL INSUFFICIENCY ASSOCIATED WITH DEFECTIVE PLACENTAL MATURATION

CROSS REFERENCE TO A RELATED APPLICATION

This application is a National Stage Application of International Application Number PCT/EP2012/064354, filed Jul. 20, 2012; which claims priority to European Patent Application No. 11006020.9, filed Jul. 22, 2011; both of which are incorporated herein by reference in their entirety.

The Sequence Listing for this application is labeled "SeqList-17Jan14.txt", which was created on Jan. 17, 2014, and is 3 KB. The entire content of the sequence listing is incorporated herein by reference in its entirety.

The present invention relates to a method for the early diagnosis of a clinically latent placental insufficiency in pathological placental maturation, and the prophylaxis of an intrauterine hypoxia/asphyxia at the due date or after a prolonged gestation, comprising determining the amount and/or the concentration of the biomarker prokineticin 1 (EG-VEGF) and/or its receptor PKR1 and/or PKR2 in a sample from the pregnant subject and/or the pregnancy. I a preferred embodiment, the invention is based on determining the ratio of the amount and/or the concentration of bFGF/PK1 as a measure of current functional condition and an indicator of latent clinical problems such as placental dysfunction resulting in fetal hypoxia. For the purposes of the present invention, the references as cited herein are incorporated by reference into the description in their entireties.

BACKGROUND OF THE INVENTION

Defective placental maturation (syn.: maturitas retarda, lack of terminal villi, retardation of the maturation of villi, arrest of the maturation of villi, placental dysmaturity, placental maturation defect, defective placental maturation) is a normally idiopathic distortion of the development of the villi, or the placental vascularization, respectively, with a latently impaired diffusion capacity of the placenta and clinically unexpected antenatal decompensation with rapidly progressive hypoxia (11, 19, 20, 21, 25).

Defective placental maturation is associated with placental restricted functional capacity and adverse perinatal fetal outcomes. An adequate capillarization is an essential factor for placental maturation and diffusing capacity.

Two main types of disturbances to placental maturation are known and these are termed delayed and accelerated maturation. Delayed maturation or villous immaturity is characterized by the deficiency of the terminal villi and limited diffusion due to a reduction in the capillary volume fraction. In 63% of the cases, an intrauterine fetal hypoxia is correlated with the villous immaturity (28). The severe form of defective placental maturation correlates with a high incidence of macrosomy (48%), intrauterine/subpartal hypoxia (38%), intrauterine death (9%) and increased neonatal mortality (5%) (1, 25).

Accelerated maturation or villous hypermaturity is characterized by a deficiency of immature intermediate villi and a predominant differentiation of terminal villi, resulting in an intensive diffusive transport efficiency. About 50% of preterm deliveries are associated with this defect of maturity (25).

Important risk factors of defective placental maturation are diabetes mellitus type 1 and type 2, gestation diabetes, adipositas, steroid therapy and viral infections of the mother, incompatibility of blood types, and prolonged gestation (11, 20, 25).

Until today, only one effective method for a prediction of the defective placental maturation or hypoxia, respectively, is available, namely the obstetrical Doppler-sonography of the umbilical arteries (7, 8, 15). Nevertheless, this method has several disadvantages:

An inhomogeneous evaluation of the results by the attending physician depending on the level of experience;

performing the method for evaluating the placental function usually only occurs in case of risk pregnancies (16, 27);

A controversial evaluation of the results in "low-risk" births at the due date and due date overruns in the context of a monitoring (26).

The placental maturity involving the development of numerous terminal villi (capillary network) and the formation of syncytiocapillary membranes for an optimal fetomaternal and maternofetal exchange of compounds is regulated by a series of angiogenetically effective factors and their related receptors (11).

Prokineticin 1, or "endocrine gland-derived vascular endothelial growth factor", (also designated as EG-VEGF, PROK1, PK1 or PRK1), and its receptors PKR1 and PKR2 have been described as possible diagnostic marker in the context of the diagnosis of OHSS syndrome (31). According to more recent results, the pro-angiogenic growth factor prokineticin-1 (PK1) is involved as an essential marker in the control of the angiogenesis in reproduction specific endocrinically active tissues (32, 33, 35, 36).

The placental prokineticin 1 is a water-soluble protein which both in its structure and function is related to the growth factor VEGF (30). The activity of PK1 is mediated by the receptors PKR1 and PKR2.

An other major positive regulator of placental vascularisation is the basic fibroblastic growth factor (bFGF). bFGF is a known endothelial mitogen and angiogenic factor in vitro. It is crucial for embryonic development, mesoderm activation, and differentiation of angioblasts into the mature endothelial cells (37). bFGF mRNA expression is associated with syncytiotrophoblasts and cytotrophoblasts of the first trimester human placenta. Syncytiotrophoblast, vascular endothelium and vascular smooth muscle cells express bFGF mRNA in the term placenta (38).

Shaw et al (in Shaw J L et al, Evidence of prokineticin dysregulation in fallopian tube from women with ectopic pregnancy. Fertil Steril. 2010 October; 94(5):1601-8.e1. Epub 2010 Jan. 4) describe tissue analysis from women who are not pregnant and women with ectopic pregnancy (EP) to demonstrate expression and regulation of prokineticins (PROKs) and their receptors (PROKRs) in fallopian tube (FT). Quantitative reverse transcriptase-polymerase chain reaction (RT-PCR) and immunohistochemistry were used to determine FT PROK/PROKR messenger RNA (mRNA) expression and protein localization, respectively. The PROK/PROKR levels were measured in tubal explant cultures stimulated with estrogen (E) and progestogen. The FT PROK2 and PROKR1 mRNA levels were up-regulated during the P-dominant midluteal phase of the menstrual cycle. Increased PROKR1 expression was observed in tubal explant cultures treated with medroxy-progesterone acetate (MPA). The PROK and PROKR proteins were localized to the epithelium and smooth muscle layers of the FT. The PROKR1 and PROKR2 mRNA levels were lower in FT from women with EP compared with non-pregnant FT from the midluteal phase. These data suggest a potential role for PROKs in FT function.

Catalano et al. (in Catalano et al. Prokineticins: novel mediators of inflammatory and contractile pathways at parturition? Mol Hum Reprod. 2010 May; 16(5):311-9. Epub 2010 Feb. 19) describe two proteins called prokineticins and the role they may play in labour and its premature onset. Prokineticin 1 and 2 bind to two G-protein coupled receptors, called prokineticin receptor 1 and 2. Expression of the prokineticins and their receptors is elevated in the uteroplacental unit during labour and they can induce expression of a host of genes known to be important in initiating the inflammatory and contractile events of labour. Prokineticins have also been shown to directly induce contractility of smooth muscles. Analysing the promoter regions of the prokineticins and their receptors highlights their potential regulation by pathways activated by infectious agents. They propose that infection can result in premature activation of prokineticin expression and signalling in the uteroplacental unit and this initiates a premature inflammatory and contractile cascade leading to preterm birth. Antagonism of prokineticin action may provide a suitable therapy for preterm labour that targets both inflammation and contractile pathways.

Hoffmann et al. (in Hoffmann et al. Expression and oxygen regulation of endocrine gland-derived vascular endothelial growth factor/prokineticin-1 and its receptors in human placenta during early pregnancy. Endocrinology. 2006 April; 147(4):1675-84. Epub 2005 Dec. 29) describe that a new angiogenic factor, endocrine gland-derived VEGF (EG-VEGF), also known as prokineticin 1 (PK1), has been identified, and its expression was shown to be restricted to endocrine glands, including the placenta. In this study they investigated the pattern of expression of EG-VEGF, its related factor Bv8/PK2, and their common receptors, PKR1 and PKR2, in human placenta during the first trimester of pregnancy. In isolated trophoblast cells (TCs), PKR1 mRNA is about 80 times more abundant than PKR2 mRNA. Both EG-VEGF and PKR1 mRNAs appear to be regulated by hypoxia. These findings suggest that EG-VEGF has a direct effect on TCs via its receptor PKR1 and is likely to play an important role in human placentation.

Recently, a diagnostic kit for the ELISA-prokineticin 1-diagnosis became commercially available.

The obstetrical Doppler-sonography can identify presymptomatic fetal moments of danger that are related to the vascularization of the placenta or defective placental maturation, respectively (5, 7, 8, 17). The high-risk group of pregnant subjects experiences a decrease of the perinatal mortality by 38-50%, without an increased rate of intervention.

Therefore, until now there are no reliable diagnostic methods in the prenatal care, and no laboratory markers for detecting the risks of placental hypoxia, in particular in pregnant women that are regarded as belonging to the "low-risk"-group (4, 20).

It is therefore an object of the present invention to provide such a diagnostic method for being able to make an early and reliable statement about a latently impaired diffusion capacity of the placenta or a functionally inadequate deficient fetal vasculature of the placenta in a defective placental maturation. Additional objects and aspects can be derived from reading the following description of the invention.

According to a first aspect of the present invention, this object is solved by a method for detecting a placental dysmaturity, wherein said method comprises determining the amount and/or expression and/or protein structure (polymorphism) of prokineticin 1 and/or its receptor PKR1 and/or PKR2 in a biological sample from a pregnant subject to be examined, and/or from a pregnancy (e.g. placenta, amniotic fluid, fetus). A reduced amount and/or expression and/or polymorphisms of prokineticin 1 and/or its receptor PKR1 and/or PKR2 in the sample as examined indicates an insufficiently developed fetal vasculature (organ-specific hypocapillarization) of the placental villi in the sense of a defective fetoplacental maturation (limited diffusion capacity). Thereby, the sample to be examined can either be compared with an autologous sample (e.g. taken earlier) or a sample from a healthy pregnant subject (or by means of a reference value as determined with healthy pregnant subjects). Healthy pregnant subject shall mean a pregnant subject having an appropriate placental maturity at the given point in time.

Preferred is a method for detecting a clinically latent placental insufficiency according to the present invention, wherein furthermore the ratio of the amount and/or expression of prokineticin 1 and bFGF is determined, and wherein a ratio based on bFGF>PK1 indicates a placental immaturity (organ-specific hypocapillarization), and a ratio based on bFGF<PK1 indicates a placental hypermaturity (organ-specific hypercapillarization).

The subject is a mammalian subject, such as, for example, a mouse, rat, monkey or human, and preferably is a human female subject.

The present invention thus solves the problem of an early diagnosis of the placental insufficiency, defective fetoplacental maturation, and possible prophylaxis and therapy of intrauterine hypoxia/asphyxia in the late pregnancy at the due date, and during prolonged gestation.

A reduced amount and/or expression of prokineticin 1 and/or its receptor PKR1 and/or PKR2 in the biological sample indicates an insufficiently developed fetal vasculature (organ-specific hypocapillarization), of the placental villi in the sense of a fetoplacental dysmaturity with an associated increased higher risk of an intrauterine, in particular antepartal, hypoxia. The results as presented particularly show the significant and dramatic reduction of the expression of prokineticin 1 (EG-VEGF; PK1) and its receptor PKR2 in the immature placentas exhibiting the severe form of antenatal fetal hypoxia.

The present invention particularly differs from the state from the art in that the amount and/or expression of PK1, PKR2, bFGF/PK1 in samples derived from the mother indicate adaptation disorders of the fetus (newborn)(the placenta is an fetal organ). Furthermore, the amount and/or expression of placental PK1, PKR2, and/or bFGF/PK1 in samples from the mother indicate a clinically latent disorder of the placental development of the placenta (dysmaturity), fetoplacental organ-specific hypocapillarization and reduction of the diffusion capacity of the placenta, with a fetal risk, fetal misregulation, fetal adaptation-disorders, fetal immaturity, aberrant fetal programming in the late pregnancy in "clinically healthy" pregnancies. Also, placental PK1 and PKR2 in samples of the mother in the late pregnancy are indicative for the placental development of the fetal organ specific capillaries, the diffusion capacity of the placenta and maturation of the adaptation processes of the child (maturation and activation of the fetal stress-axis, fetal hematopoiesis and "postnatal" vasculogenesis. bFGF indicates the development of the placental blood vessels of perfusion type and growth potential of the placenta and the child.

Finally, the quotient of bFGF/PK1 (perfusion capacity/diffusion capacity) was found to be optimal for the functional analysis of the placenta. bFGF/PK1 shows the balance between growth (bFGF) and maturation (PK1). Placental PK1 and bFGF pathogenetically reflect the activation of the fetal stress-axis, of the vasculogenesis from "postnatal" type and the adaptation fetoplacental. Intrauterine development of metabolically active fetal capillaries (PKR2) can determine the degree of metabolic processes in postnatal period ("fetal programming").

Preferred is a method according to the present invention, wherein the biological sample is a body fluid sample, such as, for example, amniotic fluid, blood, serum, saliva, urine or vaginal fluid, or a solid sample, such as, for example a tissue sample, such as, for example, a placental tissue sample. The sample can be a freshly taken sample or a conserved (e.g. frozen) or prepared (e.g. tissue section) sample.

Further preferred is a method according to the present invention, wherein the pregnant subject to be examined exhibits factors for a risk pregnancy, such as, for example, diabetes type I and type II, gestation diabetes, adipositas, prolonged gestation, endocrine disease, Rhesus- or blood type incompatibility, in vitro fertilization, progressed age, steroid therapy and/or nicotine abuse (e.g. smoking).

In general, in the context of the present invention every method for determining the amount and/or the concentration is suitable that can be applied to the respective sample. Preferably, such a method comprises PCR, real time PCR (rtPCR), quantitative PCR (qPCR), ELISA, other antibody detection methods, chromatographies, centrifugation, sequencing, mutation analysis or polymorphism-analyses (34) and/or an mRNA-detection method. Polymorphisms are described, for example, in Su et al. (Su M T, Lin S H, Lee I W, Chen Y C, Hsu C C, Pan H A, Kuo P L. Polymorphisms of endocrine gland-derived vascular endothelial growth factor gene and its receptor genes are associated with recurrent pregnancy loss. Hum Reprod. 2010 November; 25(11): 2923-30. Epub 2010 Sep. 16), or referred to in the databases as rs7514102, rs59863268, and rs17628376.

According to the invention, also genetic abnormalities or pathological polymorphisms of the gene for prokineticin 1 and/or the gene for PKR1 or PKR2 can be determined in the sample of the pregnant subject (see e.g. Su M T, et al. Polymorphisms of endocrine gland-derived vascular endothelial growth factor gene and its receptor genes are associated with recurrent pregnancy loss. Hum Reprod. 2010 November; 25(11):2923-30. Epub 2010 Sep. 16). Thus, a change of the amount and/or the concentration of prokineticin 1 and/or its receptor PKR1 and/or PKR2 is identified "indirectly", using their genetic basis. Thereby, a genetic abnormality of the gene prokineticin 1 and/or the gene for PKR1 or PKR2 indicates a distorted regulation of the fetoplacental angiogenesis with an insufficiently developed fetal vasculature of the placental villi in the sense of a fetoplacental dysmaturity with an associated higher risk for an intrauterine, in particular antepartal, hypoxia.

As a further step (or steps), the method for detecting a fetoplacental dysmaturity of the present invention can comprise a further detection using data derived from a Doppler-sonography. The Doppler-sonography can either be performed for a confirmation and/or several times in parallel (as a supplement) or extension for the method according to the present invention. Regarding this, see also further below.

As mentioned above, a reduced amount and/or concentration of prokineticin 1 and/or its receptor PKR1 and/or PKR2 in the sample indicates an insufficiently developed fetal vasculature of the placental villi in the sense of a placental insufficiency. The ratio of the amount and/or expression of prokineticin 1 and bFGF is also indicative of a placental insufficiency. Thus, particularly preferred is a method according to the present invention, wherein the amount and/or the concentration of the marker as determined in the sample is reduced by at least a factor of 2, preferably a factor of 4, when compared with a sample from a healthy pregnant subject.

Further preferred is a method according to the present invention, wherein the pregnant subject to be examined stems from a non-preselected group of pregnant subjects. This means that for the first time the method of the invention makes it possible to perform serial examinations. This will allow for the identification of yet unrecognized diseases and thus ultimately makes a prophylaxis of intrauterine hypoxia/asphyxia at the due date and in prolonged gestation possible.

A further aspect of the present invention then relates to a method for monitoring a risk-pregnancy, comprising a method according to the present invention as described above and the step (or steps) of an additional monitoring of the pregnant subject by means of data derived from a Doppler-sonography. Thus, here advantageously the combination of the present invention with known methods is used.

A further aspect of the present invention then relates to a method for determining the risk of an intrauterine, in particular antepartal, hypoxia in a pregnant subject, comprising detecting a placental insufficiency according to a method according to the present invention as described above and a subsequent determination of the risk using the data as obtained, such as, for example, the bFGF/PK1-ratio. In case of a placental insufficiency as found, the risk is increased.

The method can furthermore comprise an identification of the risk of a recurrence of a fetal hypoxia in the next pregnancy/pregnancies in case of a condition following intrauterine death which is also based on the method as described here, and the use of data as accordingly obtained. This represents a preferred example of preventive diagnostic on the basis of the invention.

A still further aspect of the present then relates to a method for determining a risk-adapted due date in a pregnant subject, comprising a method according to the present invention as described above and determining of a minimal-risk due date in a pregnant subject that was detected to have a latent placental insufficiency in form of a placental dysmaturity. Preferred is such a method according to the present invention, wherein in case of an identified additional risk for a placental insufficiency the due-date is set beginning from the 35$^{th}$ week of pregnancy. Thereby, after this point in time the risk for a hypoxia can be markedly reduced.

A further aspect of the present invention then relates to a method for treating a placental insufficiency involving a latent placental insufficiency, comprising a method according to the present invention as described above and a treatment of a placental dysmaturity as detected by means of suitable medicaments, e.g. hormones or insulin or heparin therapy. The outcome-dependent stimulation of PKS and bFGF may be a useful strategy for therapeutic fetoplacental neovascularization. This aspect relates to the direct treatment of the placental dysmaturity on the basis of the diagnosis by the attending physician.

A still further aspect of the present invention then relates to a method for treating a risk-pregnancy, comprising a method according to the present invention as described above and an additional treatment of the underlying disease by means of suitable medicaments. By "underlying disease" the secondary disease or condition of the pregnant subject shall be understood, such as, for example diabetes type I and type II, gestation diabetes, adipositas, prolonged gestation, condition following intrauterine death, endocrine disease, Rhesus- or blood type incompatibility, in vitro fertilization, progressed age, steroid therapy and/or nicotine abuse (e.g. smoking). Preferably, the disease is selected from gestation diabetes or blood type incompatibility. Of course, also mixed direct and indirect treatment schemes are contemplated by the invention.

The treatment methods according to the present invention as a further step (or steps) can comprise a further detection using data obtained from a Doppler-sonography. The Doppler-sonography can either be performed for a confirmation and/or can be performed one or several times in parallel (as a supplement) or as an extension for the method according to the present invention.

A still further aspect of the present invention then relates to a method for monitoring the medicamentous therapy of a risk-pregnancy, comprising performing the method according to the present invention as described above on a sample of a pregnant subject which undergoes a respective medicamentous therapy. This "monitoring" of the development of the fetal placental vessels can be performed, for example, in several temporally spaced samples as a continuous monitoring.

The method according to the invention for monitoring the medicamentous therapy of the risk-pregnancy as a further step (or steps) can comprise an additional detection using data from a Doppler-sonography. The Doppler-sonography can either be performed for a confirmation and/or can be performed one or several times in parallel (as a supplement) or as an extension for the method according to the present invention.

A still further aspect of the present invention then relates to the use of a diagnostic kit for the prokineticin 1-diagnosis, optionally together with bFGF, and/or the diagnosis of the receptor PKR1 and/or PKR2 in a sample in a method according to the present invention. The kit can contain respective materials for e.g. ELISA or oligonucleotides for the PCR, together with buffers and corresponding other auxiliary agents, as well as manuals and evaluation documentation. Preferred is a point of care (POC)-test kit.

A further aspect of the present invention then relates to a method for identifying a compound that influences placental dysmaturity in a pregnant subject, comprising performing a method according to the present invention as described here on a sample that was obtained from said pregnant subject and/or the pregnancy before the administration of the compound to be tested, and comparing of said sample with a sample that was obtained from said pregnant subject and/or the pregnancy after the administration of the compound to be tested, wherein a change of the amount and/or the expression of prokineticin 1, optionally together with a change of the amount and/or the expression of bFGF, and/or the receptor PKR1 and/or PKR2 indicates a compound which influences placental dysmaturity in a pregnant subject.

Preferred is a method for identifying a compound that influences placental dysmaturity in a pregnant subject according to the present invention, wherein the placental dysmaturity is influenced through influencing/modifying of the activity of prokineticin 1, optionally together with a change of the amount and/or the expression of bFGF, and/or the receptor PKR1 and/or PKR2. This activity of prokineticin 1, bFGF, and/or the receptor PKR1 and/or PKR2 can be the biological and/or biochemical activity, or the expression of the gene/s that encode for prokineticin 1 and/or its receptor PKR1 and/or PKR2. The compound can be an agonist or antagonist of the activity. Preferred is an agonist that increases the activity of prokineticin 1 and/or its receptor PKR1 and/or PKR2, and decreases the activity of bFGF.

The term "antagonist" is used herein in its broadest sense and includes every molecule that partially or completely blocks, inhibits or neutralizes the biological and/or biochemical activity of the prokineticin 1 and/or its receptor PKR1 and/or PKR2, or bFGF. In a similar manner, also the term "agonist" is used herein in its broadest sense and includes every molecule that mimics or promotes the biological and/or biochemical activity of the prokineticin 1 and/or its receptor PKR1 and/or PKR2, or bFGF. Suitable agonists or antagonists-molecules include specific agonist- or antagonist-antibodies or antibody-fragments, fragments of prokineticin 1 and/or its receptor PKR1 and/or PKR2 or bFGF, antisense oligonucleotides, small organic molecules, etc. Methods for identifying agonists or antagonists of prokineticin 1 and/or its receptor PKR1 and/or PKR2 or bFGF can comprise a contacting of the polypeptide for prokineticin 1 and/or its receptor PKR1 and/or PKR2 or bFGF with a candidate-agonist- or antagonist-molecule, and measuring and/or detecting a change in one or several biological activities, such as, for example, the maturity of villi.

Preferred is a method for identifying a compound that influences placental dysmaturity in a pregnant subject according to the present invention, wherein said measuring and/or detecting the change in one or several biological activities by means of expression comprises the use of an antibody against prokineticin 1 and/or its receptor PKR1 and/or PKR2 or bFGF, and/or an RT-PCR and/or other tests, as described above for the diagnosis.

The present invention solves the problem of a particularly early diagnosis of latent placental insufficiency in pathological placental dysmaturity and the possible prophylaxis of intrauterine hypoxia/asphyxia at the due date and upon prolonged gestation.

A reduced amount and/or concentration of prokineticin 1 and/or its receptor PKR1 and/or PKR2 indicate an insufficiently developed fetal vasculature (hypocapillarization) of the placental villi in the sense of a placental dysmaturity with an increased fetal risk of an intrauterine, in particular antepartal, hypoxia.

The present invention furthermore allows for
a) establishing of new screening methods for an early identification of a risk of placental hypoxia—also in comparison to other methods—in unselected, that is not preselected, groups of pregnant subjects,
b) the safe and early diagnosis of the latent placental insufficiency or placental dysmaturity using quantitative methods, as a support for the risk-adapted induction of birth or selection, also with prolonged gestation (23),
c) the monitoring of preventive strategies and the control of the progression of the therapy in risk pregnancies, in particular in diabetes mellitus, gestation diabetes, other endocrine maternal diseases, adipositas, prolonged gestation, Rhesus- or blood group incompatibility, in vitro fertilization, progressed age, steroid therapy and/or nicotine abuse, and
d) new specific treatment concepts for improving the fetoplacental function and optimal extension/progression of the pregnancy.

Thus, the invention for the first time, also in the context of a screening of patients, allows the simple, safe and early identification of pregnant women that during pregnancy are at a high risk to develop a "respiratory" insufficiency of the placenta with hypoxic damage to the unborn child.

The introduction of a test for prokineticin 1 and/or its receptor PKR1 and/or PKR2 for the routine-diagnosis leads to new possibilities in the prophylaxis of fetal hypoxia/asphyxia or emergency caesarean section with a decrease of the perinatal mortality and morbidity as well as an avoidance of irreversible damage to the organs of the children, in particular brain damage (24).

On the basis of the detection according to the present invention, the physician is thus able to:
Early detect pregnant subjects with a high risk of a later intrauterine hypoxia, even before additional symptoms occur;

monitor those pregnancies that are fraught with a risk more closely (e.g. by Doppler-sonography) in order to achieve a safe result for both mother and child;

initiate respective treatment options (e.g. in case of gestation diabetes, blood type incompatibility);

control the effectiveness of the medicamentous therapy (e.g. insulin therapy), and Optionally, set a risk-adapted date of delivery (if additional risks for a placental insufficiency are present, a termination of the pregnancy already after the 37th week of pregnancy might have advantages for both mother and child).

Because of the large clinical importance of the antenatal intrauterine hypoxia, the method according to the present invention will improve the health care for pregnant women, improve the clinical prevention of risk-patients as identified, and also will lower costs because of a rationalization of the prevention for pregnant women, and a reduction of the substantial follow-up costs in case of children that were harmed.

The following Table 1 further summarizes the differences and advantages of the present invention, compared to the state of the art:

and PKR2 but not PKR1 in the placentas with terminal villous deficiency in comparison to the control group. In the placentas with a predominant terminal villous differentiation, PK1 and PKR2 expression was highly elevated compared to the normal placentas. The terminal villi development was reflected by the aberration of the organ-specific capillarization and diffusion capacity. Thus, the decrease of PK1/PKR2 signaling in the placenta with delayed maturation is associated with terminal villous deficiency, hypocapillarization and limited diffusion capacity. Increased PK1/PKR2 signaling in the placentae with accelerated maturation was associated with a predominance terminal villous differentiation, hypercapillarization and improved placental diffusion.

In the placenta with a defect in the maturation and aberrant PK1/PKR2 expression there seems to be an altered transfer of steroid hormones and their precursors into maternal and fetal blood. This may be the reason for the deviations of the maturation and activation of fetal hypothalamic-pituitary/sympaticus-adrenal axis, of the beginning of the fetal "postnatal" type of vasculogenesis, of the fetal steroids synthesis and, as a result, abnormalities of the fetus and

|  | Invention | Shaw 2010 | Catalano 2010 | Reference Hoffmann 2006 |
|---|---|---|---|---|
| Aim of screening | Clinically latent forms of placental insufficiency including the risk of an antenatal Hypoxia of the child | Tubar gravidity | Premature labour (premature birth) | Preeclampsia |
| Risk stratification (prevention) | Low on risk | — | heterogeneous | Risk pregnancy |
| Primary disease | Fetoplacental disease | Maternal disease | Materno-placental disease | Materno-placental disease |
| Predominance of fetal disorders | Yes | No | No | No |
| Predominance of maternal disorders | No | Yes | Yes | Yes |
| Clinical symptoms during pregnancy | Without symptoms | present | present | present |
| Week of pregnancy | III Trimester Antenatal 35-43 WOP | I Trimester Early gravidity | II-III Trimester 20-35 WOP | II-III Trimester 20-35 WOP |
| Placental insufficiency | Chronically-latent, terminally acute | Non-viable pregnancy | acute | Chronic (not latent) |
| Duration of the placental insufficiency | Months (no screening-methods) | Days | Days | Months (Screening-methods available) |
| Predominant pathological localisation | Fetoplacental Vasculature (fetal side) | Tuba uterina (mother) | Musculature of the uterus (maternal side) | Uteroplacental vasculature (maternal side) |
| Genesis of the PK1-Changes | Fetoplacental | maternal | Maternoplacental | Maternoplacental |
| PKs-Receptors | PKR2 |  |  | PKR1 |
| Effect | Reduction of the fetal capillaries and limitation of the diffusion capacity of the placenta | Increased contractivity of the musculature (Tube) | Increased contractivity of the musculature (Uterus) | Obliteration of the spiral arteries (maternal) |
| Primary type of hypoxia | Postplacental (Child) | — | Preplacental (Uterus) | Preplacental (Uterus) |

The results of the inventors show that PK1 and PKR2 are essential for the regulation of terminal villi differentiation. Observed was a significantly decreased expression of PK1 placenta maturation. This hypothesis is consistent with the results of stereological and electron microscopy studies on human placental villi.

The inventors have also determined an inverse relationship between placental capillarization and the level of the bFGF expression. Increased bFGF expression was revealed in the placentae with terminal villous deficiency and hypocapillarization. Arany et al. (1998) also observed elevated bFGF expression in the diabetic placentae caused by increased expression in syncytiotrophoblast.

In contrast, bFGF expression was decreased in the accelerated matured placentas with enlarged terminal villi differentiation and placental hypercapillarization. A direct correlation was observed between bFGF expression and immature intermediate villi differentiation and formation of resistance vessels. Thus, intermediate villous deficiency with a decrease in placental resistance vessels, and limited placental perfusion is associated with the decrease of placental bFGF signaling.

It was further found that the VEGF and PlGF expression in the placenta with delayed maturation did not differ from the control group. PlGF expression in the placenta with accelerated maturation is also comparable with the normal control tissue, but VEGF expression is decreased and this may be the cause of the decrease of the branching angiogenesis. The results support the fact that hypoxia is not a key pathogenic factor for the placental maturity disruption.

Importantly, the inventors have also shown that antenatal placental insufficiency associated with defective maturation is accompanied by an imbalance of bFGF/PK1-expression. bFGF-hyperexpression (bFGF>PK1) results in placental immaturity with a predominance of immature villi, hypocapillarization, and structurally and functionally limited diffusion. PK1-hyperexpression (bFGF<PK1) reflects placental hypermaturity with a predominance of terminal villi, hypercapillarization, and limited perfusion. The bFGF/PK1-ratio is therefore a marker of the latent clinical restrictions of the placental function causing a potential risk resulting in fetal hypoxia.

The present invention shall now be described further on the basis of the examples with reference to the accompanying figures, nevertheless, without being limited thereto.

FIG. 1 shows the pathologic villous maturation. Delayed placental maturation: (a) low power photo micrograph (H&E, 25×) demonstrates a predominance of abnormally large immature intermediate villi with immature central capillaries, (b) higher power photo micrograph (H&E, 400×) shows large distal villi with a uniform, continuous layer of villous trophoblast and an almost total lack of sinusoidal capillary transform and vasculo syncytial membrane. Accelerated placental maturation: (c) low power photo micrograph (H&E, 25×) demonstrates a predominance of numerous small mature terminal villi and deficiency of intermediate villi, (d) higher power photo micrograph (H&E, 400×) shows terminal villi with organ-specific sinusoidal capillary transform and increased formation of vasculo syncytial membrane.

Figure 2:
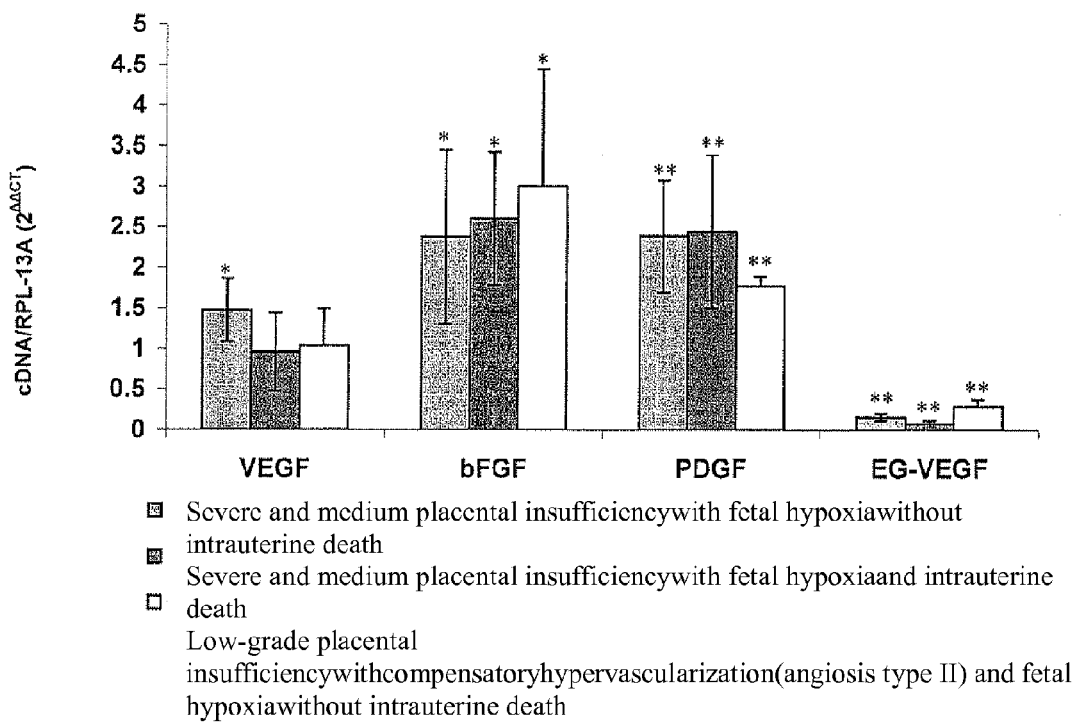

FIG. 2 shows the expression of placental angiogenic growth factors in placental dysmaturity with fetal hypoxia "at due date".

Figure 3:
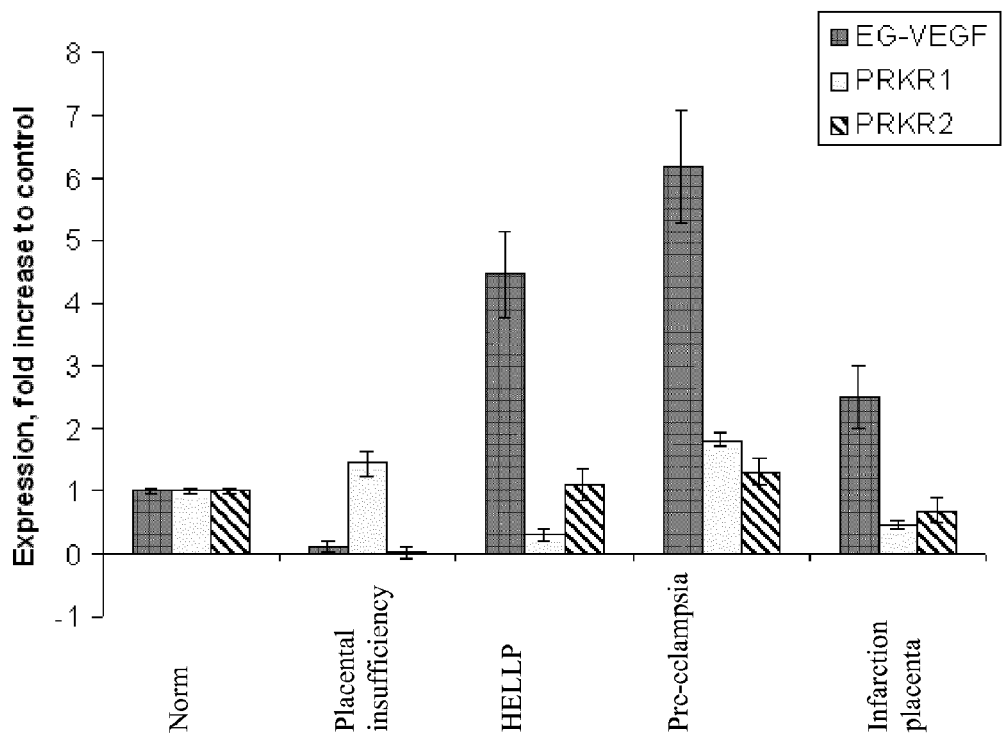

FIG. 3 shows the expression of placental EG-VEGF (prokineticin 1) and receptors PRKR1 and PRKR2 in normal pregnancies and pregnancies with fetal hypoxia at the due date: in "low risk" pregnancies with histologically proven placental dysmaturity and in "risk pregnancies" with clinically identified gestosis (HELLP-syndrome, pre-eclampsia and infarction placenta). A significant reduction of EG-VEGF (prokineticin 1) and PRKR2 in placental dysmaturity and "unremarkable" progression of the pregnancy (placental insufficiency of unclear origin). Reduction of PRKR1 can be found in severe gestosis (HELLP-syndrome).

Figure 4:
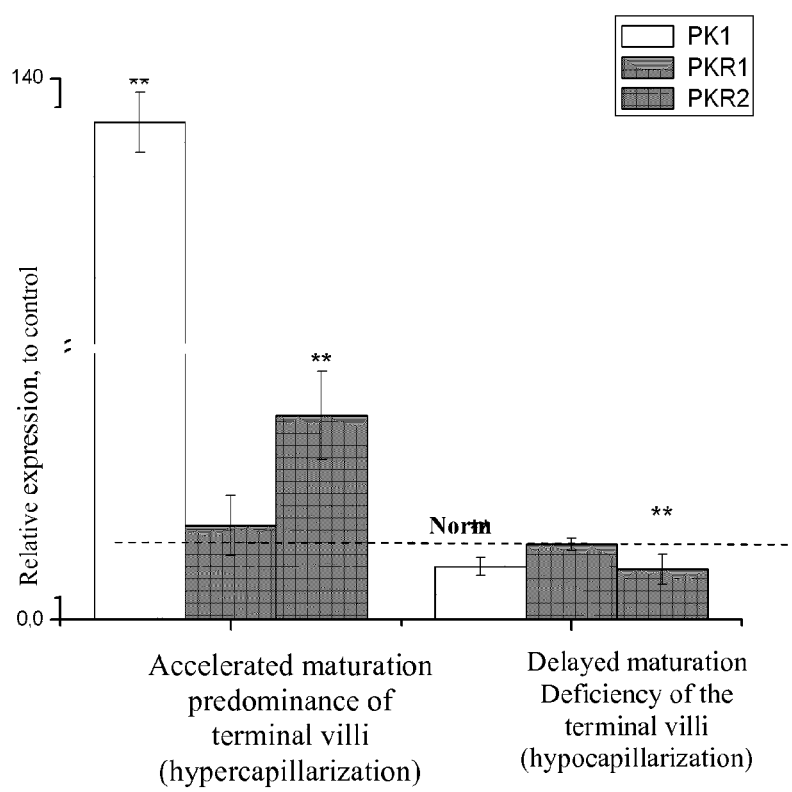

FIG. 4 shows another example of the expression of PK1, PKR1 and PKR2 mRNA in human placentas from the end of $3^{rd}$ trimester determined by qPCR according to the examples. To determine the relative quantification of gene expression for both target and housekeeping genes, the comparative ddCt method was used. As an internal PCR control for sample loading and normalization the housekeeping genes GAPDH or RPL13A were used.

Figure 5:
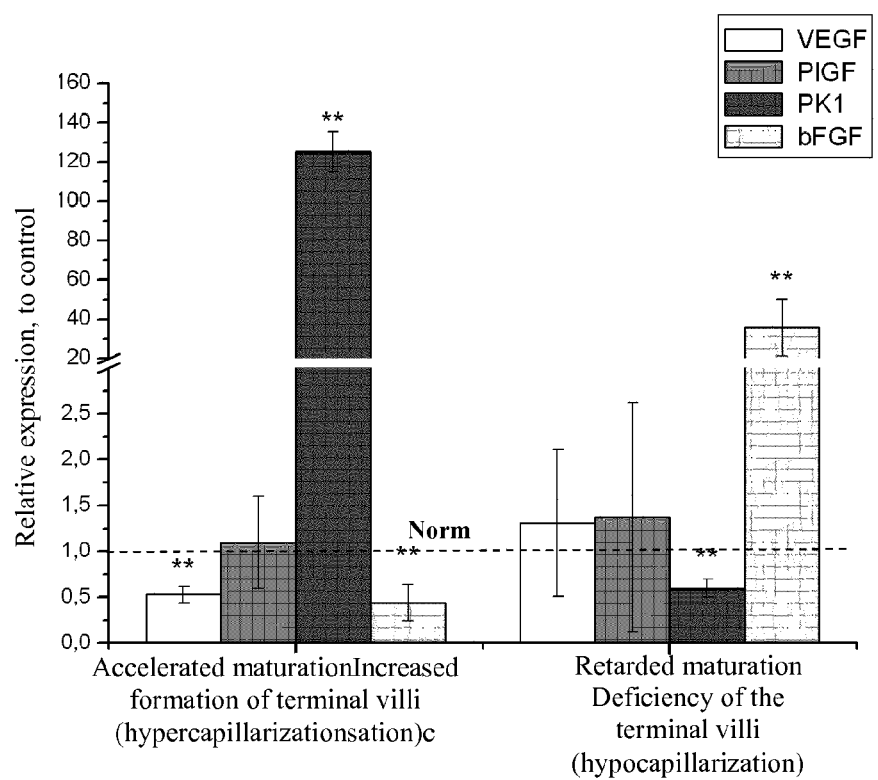

FIG. 5 shows the expression of VEFG, PlGF, PK1 and bFGF in third trimester placenta with delayed and accelerated villous maturation. To determine the relative quantification of gene expression for both target and housekeeping genes, the comparative ddCt method was used. As an internal PCR control for sample loading and normalization the housekeeping genes GAPDH or RPL13A were used.

EXAMPLES

The expression of placental angiogenic growth factors in placental insufficiency with fetal hypoxia "at the due date" was determined in 60 pregnant subjects (n=60) (see FIGS. 1 and 2).

For this, a quantification of mRNA was performed by means of real-time PCT (qPCR) using the delta-delta-Ct method with RPL-13A as a reference gene.

The placental insufficiency was graded according to its quality into three clinical-morphological degrees of severity: 1. Severe and medium placental insufficiency with fetal hypoxia without intrauterine death, 2. Severe and medium placental insufficiency with fetal hypoxia and intrauterine death, 3. Low-grade placental insufficiency with compensatory hypervascularization and fetal hypoxia without intrauterine death.

Tissue Specimens and Histology

Tissue samples were obtained from term placentas, which underwent examination in the Department of Pathology, University of Mainz. Excess material from anonymous pathomorphological tissue collected for diagnostic purposes was used for the studies. Informed consent was obtained and approved in accordance with the regulations of the Local Ethic Committee. Control placentae were collected at 37-41 weeks from uncomplicated pregnancies ending in spontaneous labour with no neonatal problems or malformations.

Tissue Deparaffinization and Total RNA Isolation

Total RNA was extracted from paraffin-embedded placental tissue. Tissue was deparaffiinized with xylol (Diagonal GmbH & Co. KG), and 100% alcohol. The alcohol was aspirated and the tissue pellet was dried (45° C., 10 or more min depending on tissue quantity), and incubated with 270 μl of digesting buffer (80° C., 10 min). This was then cooled to room temperature, briefly centrifuged, after which 30 μl of Proteinase K were added and incubated overnight at 56° C. Proteins were precipitated with 150 μl of MPC-reagent (Epicentre® Biotechnologies, USA). The phases were separated by a 10-min centrifugation at maximal speed at 4° C. The aqueous phase was transferred to a fresh tube, and an equal volume of isopropanol was added, samples were vortexed and after another 15-min centrifugation (maximal speed, 4° C.), the supernatant was carefully aspirated and discarded. After this, 1 ml of 70% ethanol was added and the tube was vortexed and recentrifuged at 4° C. for 5 min. The final pellet was dried completely in a hood and finally dissolved in 50 μl distilled water. Quantification of total nucleic acids was performed by measuring absorbance at OD260 using a NanoDrop Spectrophotometer (Thermo Scientific, Wilmington, Del., USA) and concentrations of all samples were adjusted to 100 ng/μl.

cDNA Synthesis cDNA synthesis from total RNA (11 ul) was carried out in a reaction volume of 25 μl containing 50 mM Tris-HCl (pH 8•3), 70 mM KCl, 3 mM MgCl2, 10 mM dithiothreitol, 5 μM random hexamer primer, 27 mM deoxynucleoside tri-phosphate, 2 units/μl RNasin Plus RNase Inhibitor and 8 units/μl M-MLV Reverse Transcriptase (all reagents obtained from Promega). RNA was initially denatured at 70° C. for 5 min. The reaction mixture was then added and reverse transcription was performed at 40° C. for 60 min. The cDNA was stored at −20° C. Negative control was prepared as described above, but without RNA sample.

Quantitative Real Time PCR (qPCR)

cDNA was amplified with 2× Power SYBR Green PCR Master Mix (Applied Biosystems) using Applied Biosystems 7300 Real-Time PCR System. cDNA was denatured in 96-well-plate at 95° C. for 10 min before the first PCR cycle. The following thermal run protocol was used: denaturation program (95° C. for 10 min), amplification and quantification program repeated 40 times (95° C. for 15 s, 60° C. for 60 s) (40 cycles). Melt curve analysis was performed to confirm the specificity of the amplified products. All samples were run in triplicate, and relative expression was determined by normalizing samples to RPL13A housekeeping gene. Data were analyzed using the comparative Ct method (ddCt) [17]. Primers were designed using the primer design software PrimerQuest (Integrated DNA Technologies, Inc., USA). Details of the primers are given in Table 2. Self-designed primers were synthesised by Microsynth AG (Balgach, Switzerland) or Eurofins MWG Operon (Ebersberg, Germany).

TABLE 2

Primers used for quantitative PCR

| Gene | | Forward primer | |
|---|---|---|---|
| GAPDH | | | |
| | sense | 5'-ATGGGGAAGGTGAAGGTCG-3' | (SEQ ID No. 1) |
| | antisense | 5'-TAAAAGCAGCCCTGGTGACC-3' | (SEQ ID No. 2) |
| RPL13A | | | |
| | sense | 5'-CCTGGAGGAGAAGAGGAAAGAGA-3' | (SEQ ID No. 3) |
| | antisense | 5'-TTCGTAGCCTCATGAGCTGTT-3' | (SEQ ID No. 4) |
| VEGFA | | | |
| | sense | 5'-CGAGGGCCTGGAGTGTGT-3' | (SEQ ID No. 5) |
| | antisense | 5'-CCGCATAATCTGGATGGTGAT-3' | (SEQ ID No. 6) |
| FGF2 | | | |
| | sense | 5'-CCGTTACCTGCCTATGAAGGAA-3' | (SEQ ID No. 7) |
| | antisense | 5'-AAAGAAACACTCATCCGTAACACATT-3' | (SEQ ID No. 8) |
| PlGF | | | |
| | sense | 5'-GCGATGAGAATCTGCACTGTGT-3' | (SEQ ID No. 9) |
| | antisense | 5'-TCCCCAGAACGGATCTTTAGG-3' | (SEQ ID No. 10) |
| PROK1 | | | |
| | sense | 5'-CGCGAGTCTCAATCATGCTCCT-3' | (SEQ ID No. 11) |
| | antisense | 5'-GGCAAGGCGCTAAAAATTGATG-3' | (SEQ ID No. 12) |
| PROKR1 | | | |
| | sense | 5'-TGCCTTCTACATCGTCCAGTGCAT-3' | (SEQ ID No. 13) |
| | antisense | 5'-TGTAAGAAGCCTTCCAGTGGAGCA-3' | (SEQ ID No. 14) |
| PROKR2 | | | |
| | sense | 5'-TCTGCGGCATCGGTAACTTTGTCT-3' | (SEQ ID No. 15) |
| | antisense | 5'-CAGGTTGGCAATGAGCAGATTGGT-3' | (SEQ ID No. 16) |

Statistical Analysis

Results were expressed as mean±standard error of the mean. Group-wise comparison and statistical analysis of relative expression results were performed using REST 2009 Software (QIAGEN). The efficiency of the PCR reaction for each sample was calculated with the help of "LinRegPCR" program. The mean efficiency for each amplicon group (the group of samples in which the same pair of primers was used) was applied for further analysis. A range of median efficiency from 1.78 to 1.88 was allowed. The limit of significance was set at a p value of ≤0.05.

Results

Macroscopic and Histological Observations of the Placentae

FIG. 1 shows typical photo of the placentas with delayed maturation and accelerated maturation.

Expression of PK1, PKR1 and PKR2 in Third Trimester Placenta with Delayed and Accelerated Villous Maturation Using quantitative RT-PCR the inventors studied and compared the expression of PK1 and its receptors 1 and 2 in the placenta with delayed, accelerated and normal villous maturation. It was found that relative expression of PK1 and PKR2 mRNA was significantly lower within the group with delayed villous maturation than in normal group (FIG. 4). In contrast, in the group with villous acceleration there was significant increase of PK1 and PKR2 expression in comparison with the control group (FIG. 4). There was no significant difference in relative PKR1 mRNA expression between delayed maturation group and control group and between accelerated maturation group and control group (FIG. 4).

Expression of VEFG, PlGF, PK1 and bFGF in Third Trimester Placenta with Delayed and Accelerated Villous Maturation The inventors also compared the levels of VEGF, bFGF and PlGF mRNA expression in placental tissue from patients with delayed, accelerated maturation and norm. FIG. 5 shows decreased expression of VEGF and bFGF mRNA in the group with accelerated maturation versus control, and increased expression of bFGF mRNA in delayed maturation group versus control group. The expression of VEGF and PlGF mRNA in the placentas with delayed maturation did not differ from normal placenta (FIG. 5).

TABLE 4-continued

Comparison of normal and pathological villous maturation

| Villous maturation score (Benirschke 2006) | Normal maturation | Delayed maturation | Accelerated maturation |
|---|---|---|---|
| Placental function | | | |
| Diffusion capacity | Norm | Reduced | Increased |
| Perfusion capacity | Norm | Increased | Reduced |
| Limiting factor | No | PK1/PKR2 | bFGF |
| Stimulation factor | bFGF/PK1 | bFGF | PK1 (PK2) |
| Stimulated Cell Population | Angioblasts/ Hematopoietic stem cells | Angioblasts | Hematopoietic stem cells |
| bFGF/PK1 ratio | 1 | >>1 (59.7) | <<1 (0.003) |

LITERATURE AS CITED

1. Beinder E., Bucher H. U. Totgeburt und plötzlicher Kindstod Gynäkologe 2008 41: 283-292

TABLE 3

Results of quantitative Real-Time PCR (human placenta) according to the examples

| Group (37-41 pregnancy week) | Diffusion resource | Perfusion resource | Relative Expression (Norm 1) | | | | | |
|---|---|---|---|---|---|---|---|---|
| | | | VEGF | PK1 | PKR1 | PKR2 | bFGF | PlGF |
| Delayed maturation + unexplained antenatal placental insufficiency (fetal hypoxia) | ↓ | ↑ | 1.33 ±0.46 | ↓ 0.6** ±0.07 | 0.85 ±0.7 | ↓ 0.50** ±0.23 | ↑ 51.6** ±20.8 | 1.32 ±1.43 |
| Delayed maturation + sudden intrauterine unexplained death (extreme fetal hypoxia) | ↓ | ↑ | ↑ 1.60* ±0.81 | ↓ 0.7** ±0.05 | 0.81 ±0.6 | ↓ 0.46** ±0.20 | ↑ 32.4** ±15.6 | 0.95 ±0.51 |
| Delayed maturation + unexplained antenatal placental insufficiency (fetal hypoxia) + sudden intrauterine unexplained death (extreme fetal hypoxia) | ↓ | ↑ | 1.31 ±0.8 | ↓ 0.6** ±0.1 | 0.85 ±0.7 | ↓ 0.57** ±0.17 | ↑ 35.8** ±14.3 | 1.37 ±1.25 |
| Accelerated maturation + unexplained antenatal placental insufficiency (fetal hypoxia) | ↑ | ↓ | ↓ 0.53** ±0.09 | ↑ 125.21** ±10.15 | 1.06 ±0.34 | ↑ 2.3** ±0.5 | ↓ 0.44** ±0.2 | 1.1 ±0.5 |

TABLE 4

Comparison of normal and pathological villous maturation

| Villous maturation score (Benirschke 2006) | Normal maturation | Delayed maturation | Accelerated maturation |
|---|---|---|---|
| Villous development | | | |
| Terminal villi | Norm | Limited | Predominant |
| Immature intermediate villi | Norm | Predominant | Limited |
| Vascular arrangement | | | |
| Organ-specificcapillaries | Norm | Reduced | Increased |
| Resistance vessels | Norm | Increased | Reduced |

2. Catalin S. Buhimschi, M D et al Urinary angiogenic factors cluster hypertensive disorders and identify women with severe preeclampsia American Journal of Obstetrics and Gynecology (2005) 192, 734-41
3. Drommelschmidt K Placentalgrowthfactor (PLGF): -Ein prädiktiver Marker für Präeklampsie Z Geburtshilfe Neonatol 2009:213
4. Dückelmann A. Dudenhausen J. W. Kalache K. D. Effiziente Schwangerenvorsorge durch korrekte Diagnose von "Befundrisiken" Gynäkologe 2009.42:93-101
5. Ertan A. K., He J. P. et al. Placental Morphometry in Pregnancies with Reversed Enddiastoloc Flow in the Umbilical Artery or Fötal Aorta. Z Geburtshilfe Neanatol 2003; 207(5): 173-178

6. Franz M. B., Husslein P. W., Zeisler H. Neue Methoden zur Früherkennung der Präeklampsie. Gynäkologie 2009.42:872-876
7. Hitschold T., Weiss E., Beck T. et al (1989) Gepulste Dopplersonographie der Nabelarterie und fetoplazentarer Wiederstand. Geburtsh Frauenheilk 49:1056-1067
8. Hitschold T., Weiss E. et al. Beeinflußt die Vaskularisation der Placenta fetalis die enddiastolischen Blutflußgeschwindigkeiten in den Nabelarterien? Geburtsh Frauenheilk 1990; 50(8):623-627
9. Horn L. C.; Purz, S.; Stepan, H.; Viehweg, B.; Faber, R.: Sudden intrauterine unexplained death syndrome (SI-UDS): Fetal and placental autopsy is strongly recommended for evaluating the cause of pregnancy failure Geburtsh Frauenheilk 2005; 66: P1-6
10. Horn, L. C.; Purz, S.; Stepan, H.; Viehweg, B.; Faber, R.: Sudden intrauterine unexplained death syndrome (SI-UDS) is mainly caused by placental dysmaturity Z Geburtshilfe Neonatol 2005; 209: P 5-7
11. Kaufmann P. Kertschanska S. Frank H.-G. Morphologische und zellbiologische Grundlagen der sog. Plazentainsuffizienz Reproduktionsmedizin 2000 16:405-419 (416-417!)
12. Mires G J, Christie A D, Leslie J, et al.: Are notched uterine arterial waveforms of prognostic value for hypertensive and growth disorders of pregnancy? Fötal DiagnTher 10 (1995) 111-118.
13. Neilson J P: Doppler ultra sound in high risk pregnancies. In: Einkin M W, Keirse M J N C, Renfrew M J, Neilson J P (eds.): Pregnancy and childbirth module. Update software disk issue 1, Oxford 1995
14. Paciencia M, Dolley P et al Acute-placental dysfunction by villous-maturation defect late-fötal mortality. J Gynecol Obstet Biol Reprod (Paris) 2008 October; 37 (6): 602-7
15. Prtilo A., Beinder E., Stallmach T. Sonomorphologie der Plazenta und Endzottenmangel. Z. Geburtshilfe Neonatol 2007; 211
16. Richtlinien des G-BA über die ärztliche Betreuung während der Schwangerschaft und nach der Entbindung vom 21.05.2010
17. Schneider K. T. M. und Gnirs J. (2006) Antepartale Überwachung. Die Geburtshilfe, IV.S.561-590
18. Steiner E. Hoffman M. et all Wiederholungsrisiko der Plazentainsuffizienz aus klinischer und morphologischer Sicht Geburtsh Frauenheilk 2001; 61: 285-289
19. Stallmach T. Examination of the placenta in late intrauterine death: What can we tell about cause cand recurrence risk? Selected topics in pediatric pathology 1999; Vol. 32, No 3 S.322.323
20. Stallmach T. Hebisch G. Rescue by Birth: Defective Placental Maturation and Late Fetal Mortality Obstetrics Gynecology 2001 Vol 97 NO 4 April: S505-509
21. Stallmach T. Hebisch G. Placental pathology: its impact on explaining prenatal and perinatal Virchows Arch (2004) 445:9-16
22. Stepan, H.; Schaarschmidt, W. et al Angiogene Faktoren zur Diagnosesicherung bei Präeklampsie in der klinischen Routine: erste Erfahrungen Z Geburtshilfe Neonatol 2010; 214: 234-238
23. Surbek D. Terminüberschreitung in der Schwangerschaft Gynäkologie 2011-1:6-12
24. Tutdibi E., Veit M., Gorthner L. Neonatologische Notfalle beim reifen Neugeborenen. Intensivmed 2011-48:7-14
25. Vogel M (1996) Atlas der morphologischen Plazenta diagnostik. 2. Auflage. Springer, Berlin Heidelberg New York (S.83 und S.112-113)
26. Weiss E. Schwangerschaft am Termin Gynäkologie 2010 43: 601-611
27. Wissler J., Kurmanavicius J. et al Sinn und Unsinn eines Doppelscreenings Perinatal Medizin (1997) 9: 22-25
28. Schweikhart G., Kaufmann P. Endzottenmangel und klinische Relevanz. Gynäk. Rdsch. 27: suppl. 2, pp. 147-148 (1987)
29. Hoffmann P., Feige J.-J., Alfaidy N. Expression and Oxygen Regulation of Endocrine Gland-Derived Vascular Endothelial Growth Factor/Prokineticin-1 and Its Receptors in Human Placenta during Early Pregnancy. Endocrinology Apr. 1, 2006 vol. 147 no. 4 1675-1684
30. Brouillet S., Hoffmann P. et al Molecular Characterization of EG-VEGF-mediated Angiogenesis: Differential Effects on Microvascular and Macrovascular Endothelial Cells. Cell Physiology Vol. 21, Issue 16, 2832-2843, Aug. 15, 2010
31. Zhao X M et al. Endocrine gland-derived vascular endothelial growth factor concentrations in follicular fluid and serum may predict ovarian hyperstimulation syndrome in women undergoing controlled ovarian hyperstimulation. Fertil Steril. 2011 February; 95(2):673-8.
32. Brouillet S., Hoffmann P. et al. Molecular Characterization of EG-VEGF-mediated Angiogenesis: Differential Effects on Microvascular and Macrovascular Endothelial Cells Mol Biol Cell. 2010 Aug. 15; 21(16): 2832-2843.
33. Hoffmann P., Feige J.-J. et al. Placental Expression of EG-VEGF and its Receptors PKR1 (Prokineticin Receptor-1) and PKR2 Throughout Mouse Gestation. Placenta 28 (2007) 1049-1058.
34. Su M., Lin S. et al Polymorphisms of endocrine gland-derived vascular endothelial growth factor gene and its receptor genes are associated with recurrent pregnancy loss. Oxford Journals Medicine Reproduction Volume 25, Issue 11 Pages. 2923-2930
35. Ngan E S, Tam P. Prokineticin-signaling pathway. The International Journal of Biochemistry & Cell Biology 40 (2008) 1679-1684.
36. Zhou Q.-Y. The Prokineticins: A Novel Pair of Regulatory Peptides Mol Interv. 2006 December; 6(6): 330-338.
37. Poole T J, Finkelstein E B, and Cox C M. The role of FGF and VEGF in angioblast induction and migration during vascular development. Dev Dyn 2001; 220: 1-17.
38. Arany E, Hill D J. Fibroblast growth factor-2 and fibroblast growth factor receptor-1 mRNA expression and peptide localization in placentae from normal and diabetic pregnancies. Placental 998; 19(2-3):133-42.

The invention claimed is:

1. A method for treating clinically latent defective placental maturation, the method comprising determining the amount and/or expression of prokineticin 1 and/or its receptor PKR1 and/or PKR2 in a biological sample from a pregnant subject, identifying the pregnant subject as having a defective placental maturation with a functionally impaired deficient fetal vasculature based on a reduced amount and/or expression of prokineticin 1 and/or its receptor PKR1 and/or PKR2 in the biological sample, and administering to the pregnant subject identified as having the defective placental maturation an appropriate treatment for treating the defective placental maturation.

2. The method according to claim 1, wherein the method further comprises determining the ratio of the amount and/or expression of prokineticin 1 to the amount and/or expression of basic fibroblastic growth factor (bFGF), and identifying the pregnant subject as having a placental immaturity based on the ratio being less than 1 and identifying the pregnant subject as having a placental hypermaturity based on the ratio being more than 1.

3. The method according to claim 1, wherein said biological sample is amniotic fluid, blood, serum, saliva, urine or vaginal fluid, or a tissue sample.

4. The method according to claim 1, wherein the pregnant subject exhibits one or more factors for a risk pregnancy.

5. The method according to claim 1, wherein the detection of the amount and/or the expression of the mRNAs for prokineticin 1 and/or its receptor PKR1 and/or PKR2 is achieved using real-time polymerase chain reaction or quantitative polymerase chain reaction.

6. The method according to claim 1, wherein the amount and/or the concentration in the sample is reduced by at least a factor of 2 when compared to a healthy pregnant subject.

7. The method according to claim 1, wherein the pregnant subject to be examined comes from a non-preselected group of pregnant subjects.

8. A method according to claim 1, wherein the method further comprises monitoring the pregnant subject by means of data derived from a Doppler-sonography.

9. A method for determining a risk of intrauterine hypoxia in a pregnant subject, comprising detecting defective placental maturation according to claim 1 and determining the risk of intrauterine hypoxia by using the data as obtained.

10. A method for determining a risk-adapted due date in a pregnant subject, comprising the method according to claim 1, and further determining a minimal-risk due date in a pregnant subject identified as having defective placental maturation.

11. The method according to claim 1, the method further comprising administering an additional treatment for an underlying disease.

12. A method for monitoring the medicamentous therapy of placental dysmaturity, comprising performing the method according to claim 1 on a sample from a pregnant subject who is subjected to a medicamentous therapy.

13. A method for identifying a compound that influences placental dysmaturity in a pregnant subject, comprising performing a method according to claim 1 on a sample that was obtained from said pregnant subject before the administration of the compound to be tested, and comparing of said sample with a sample that was obtained from said pregnant subject after the administration of the compound to be tested, wherein a change of the amount and/or the expression of prokineticin 1, optionally together with a change of the amount and/or the expression of bFGF, and/or the receptor PKR1 and/or PKR2 indicates a compound which influences placental dysmaturity in a pregnant subject.

14. The method, according to claim 4, wherein the one or more factors are selected from diabetes type I and type II, gestation diabetes, adipositas, prolonged gestation, endocrine disease, Rhesus- or blood type incompatibility, in vitro fertilization, progressed age, steroid therapy and nicotine abuse.

15. The method, according to claim 10, wherein, in the case of an identified additional risk for defective placental maturation the due-date is set beginning from the $37^{th}$ week of pregnancy.

16. The method, according to claim 11, wherein the underlying disease is gestation diabetes or blood-type incompatibility.

17. The method of claim 1, wherein the biological sample is blood or serum.

18. The method of claim 17, wherein the amount and/or expression of the mRNAs for prokineticin 1 and/or its receptor PKR1 and/or PKR2 are determined.

19. The method of claim 18, wherein the detection of the amount and/or the expression of the mRNAs for prokineticin 1 and/or its receptor PKR1 and/or PKR2 is achieved using real-time polymerase chain reaction or quantitative polymerase chain reaction.

* * * * *